United States Patent [19]

Brueckner et al.

[11] Patent Number: 5,089,659
[45] Date of Patent: Feb. 18, 1992

[54] PREPARATION OF E7/Z9-ALKADIEN-1-OLS AND THEIR DERIVATIVES PROTECTED AT THE HYDROXYL GROUP

[75] Inventors: Christiane Brueckner; Ernst Buschmann, both of Ludwigshafen; Wolfgang Mackenroth, Bad Duerkheim; Walter Himmele, Walldorf; Heinz Eckhardt, Ludwigshafen, all of Fed. Rep. of Germany

[73] Assignee: BASF Aktiengesellschaft, Ludwigshafen, Fed. Rep. of Germany

[21] Appl. No.: 354,203

[22] Filed: May 19, 1989

[30] Foreign Application Priority Data

May 21, 1988 [DE] Fed. Rep. of Germany ....... 3817399

[51] Int. Cl.$^5$ .................... C07C 67/28; C07C 27/00
[52] U.S. Cl. .................... 560/238; 568/878
[58] Field of Search .................. 560/238; 568/878

[56] References Cited

U.S. PATENT DOCUMENTS 3,845,108 10/1974 Roelofs et al. .................. 560/261

FOREIGN PATENT DOCUMENTS 2098609 5/1982 United Kingdom .

OTHER PUBLICATIONS

Liebigs Annalen Der Chemie, Sep. 1981, No. 9, Bestmann, et al., 2117–2138.
Tetrahedron Letters, No. 26, 2467–2470 (1979).
Tetrahedron Letters, vol. 21, pp. 1497–1500, Cassaui et al., "α-Pheylselenenylation of Zirconium or Aluminum Enolates", 1980.
Bulletin Society Chimique of France, 1977, pp. 941–946 Descoins et al.
Tetrahedron Letters, No. 5, pp. 411–414, 1977, Negishi et al.
Tetrahedron Letters, No. 48, pp. 4209–4212, 1975 Labovitz et al.

Primary Examiner—Jose G. Dees
Attorney, Agent, or Firm—Oblon, Spivak, McClelland, Maier & Neustadt

[57] ABSTRACT

E7/Z9-alkadien-1-ols which may be protected at the hydroxy group are prepared by subjecting a 7-hydroxyheptenal to a Wittig reaction with a phosphorylide to give an acetal compound which is converted by further Wittig reaction with a phosphorylide to an E7/Z9-alkadienol.

7 Claims, No Drawings

PREPARATION OF E7/Z9-ALKADIEN-1-OLS AND THEIR DERIVATIVES PROTECTED AT THE HYDROXYL GROUP

The present invention relates to the preparation of E7Z9-alkadien-1-ols of the general formula I

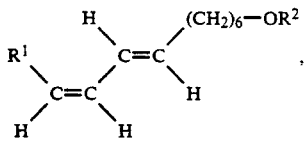

where $R^1$ is $C_1$–$C_8$-alkyl and $R^2$ is hydrogen or a base-stable protective grup.

The present invention relates in particular ot the preparation of E7/Z9-dodecadienyl acetate (where $R^1$ is $C_2H_5$ and $R^2$ is $COCH_3$), the sexual pheromone of the grape-berry moth (*Lobesia botrana*). By using this pheromone, which has an attractive and highly stimulating effect on the male animals, this pest, which is regarded as the most important insect pet in viticulture in central and, predominantly, southern Europe, can be effectively controlled (see, for example, Röhrich et al., Rev. Zool. Agric. Pathol. Veg. 76 (1977), 25).

Various methods have been described to date for the synthesis of this pheromone, which is thus of e3conomic relevance, the majority of tehse methods being based on coupling reactions ofa cetylene derivatives (Labowitz et al., Tetrahedron Lett. 1975, 4209–4212; Negishi et al., Tetrahedron Lett. 1977, 411–414; Descoins et al., Bull Soc. Chim. Fr. 1977, 941–946; Cassani et al., Tetrahedron Lett. 1980, 1497–1500). A common feature of the method sis that they use sensitive and expensive reagents which are difficult to handle and do not permit an industrial scale procedure.

Synthetic routes which have a large number of stages and therefore appear unprofitable have also been described (Roelofs et al., U.S. Pat. No. 3,845,108). French Laid-Open Application 2,505,820 has described a 4-stage process starting from 9-hydoxynonan-1-al, the last process stage involving chain extension by reaction of 9-hydroxy-2-nonenal, which may bea cylated at the OH funtion, with phosphorylides.

It is an object of the present invention to provide an economical process, which can be carried out on an industrial scale, for the preparation of E7/E9-alkadienols I, in particular those which are biologically active, such as E7/Z9-dodecadienyl acetate.

We have found that this object is achieved by a process for the preparation of E7/Z9-alkadien-1-ols of the general formula I

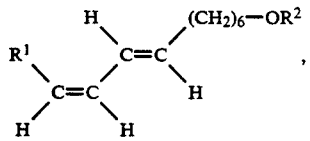

where $R^1$ is $C_1$–$C_8$-alkyl and $R^2$ is hydrogen or a base-stable alcohol protective group, wherein a 7-hydroxyheptan-1-al, which may be protected at the OH function, of the formula II

is subjected to a Wittig reaction with a phosphorylide of the general formula III

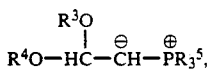

where $R^3$ and $R^4$ are each a low molecular weight alkyl group or are bonded to one naother to form an unsubstituted or $C_1$-$C_4$-alkyl-substituted dioxane or dioxolane system and $R^5$ is alkyl, cycloalkyl, phenyl or substituted phenyl, to give a compound of the general formula IV

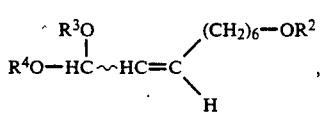

which is converted by the action of an acid into a trans-2-nonenal of the formula V

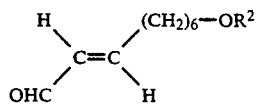

which is converted by a further Wittig reaction with a phosphorylide of the formula VI

where $R^1$ and $R^5$ have the abovementioned meanings, to an E7/E9-alkadienol I, which is obtained from the reaction mixture in a conventional manner.

The present invention describes the synthesis of the diene system of the desired pheromone by two successive Wittig reactions. The process has a short reaction path, employs readily available and economical starting materials which are easy to handle, permits an industrial scale procedure and leads predominantly to the desired stereoisomers.

The individual steps of the process are illustrated by the following reaction scheme:

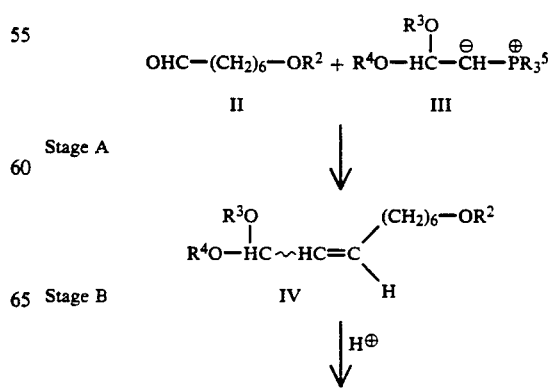

Stage A

Stage B

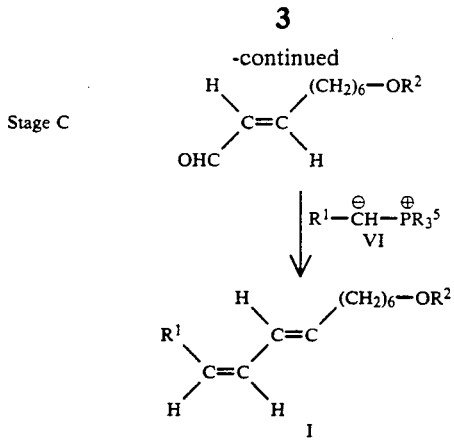

Stage C

The 7-hydroxyheptanal II, or its derivatives protected at the OH function, are known per se or can be prepared by known methods, for example as described in J. Chem. Ecol. 11 (1) (1985), 113.

Particularly suitable protective groups $R^2$ are base-stable grups, such as $C_4$-$C_{12}$-tert-alkyl groups which carry a tertiary carbon atom in the 1-position, such as tert-butyl, 1,1-dimethylprop-1yl and 1,1-dimethylbut-1-yl; $C_3$-$C_8$-trialkylsilyl groups, such as trimethylsilyl, triethylsilyl, tri-n-propylsilyl, triisopropylsilyl, tri-n-butylsilyl, dimethylethylsilyl, diethylmethylsilyl and dimethyl-n-butylsilyl; benzyl, acyls, for exmaple $C_2$-$C_4$-alkanoyls, such as acetyl, propionyl and butyryl; benzoyl; acyclic or cyclic acetal groups, such as $C_2$-$C_9$-alkoxymethoxy, $C_3$-$C_{10}$-1-alkoxyethoxy, 2-furanyl, 2-tetrahydrofuranyl, 2-pyranyl, 2-tetrahydropyranyl, 1,3-dioxan-2-yl, 1,3-dioxan-2yl and 1,4-dioxan-2-yl. Since the acetyl group is present int he pheromone of *Lobesia botrana*, this protective group is preferred.

$R^3$ and $R^4$ are each low molecular weight alkyl groups, for example branched or straight-chain $C_1$-$C_8$-alkyl, preferably $C_1$-$C_4$-alkyl, such as methyl, ethyl, propyl, isoprpyl, n-butyl, isobutyl, sec-butyl, tert-butyl, pentyl, hexyl or actyl. The two radicals $R^3$ and $R^4$ can furthermore together form an ethhylene or propylene bridge, giving a dioxane or dioxolane system.

$R^5$ is $C_1$-$C_8$-alkyl, $C_5$ or $C_6$-cycloalkyl or, in particular, unsubstituted or substituted phenyl, suitable substituents being inert groups, such as$C_1$-$C_4$-alkyl, $C_1$-$C_4$-alkoxy or halogen, such as fluorine, chlorine or bromine. Unsubstituted phenyl radicals are preferred since the starting material triphenylphosphine used for the preparation of the ylides is particularly economical and furthermore the very sluggishly reacting solid triphenylphosphine oxide, which can readily be separated off, is formed in the reactions.

The phosphorylides III and VII can be prepared in a conventional manner, for example as described in J. March, Advanced Organic Chemistry, 2nd Edition, pages 864–872, 1977 McGraw-Hill Kogakusha, Ltd., and the literature cited therein, by deprotonation of the corresponding phosphonium halides, preferably bromides or clhorides, by means of a base. The deprotonation is carried out separatedly or, advantageously, in situ in an aprotic solvent at room temperature or at aborm 0° to 100° C. (cf. J. Chem. Soc., Perkin I, 1974, 37–41). The solvents used are, for example, amides which are completely substituted at the nitrogen, such as dimethylformamide, dimethylacetamide, diethylformamide or N-methylpyrrolidone; sulfones, such as dimethyl sulfone, sulfoxides, such as dimethyl sulfoxide; ethers, such as tetrahydrofurans; glycol ethers, such as dimethoxyethane, diethoxyethane, diglyme; aromatic hydrocarbons such as benzene or toluene, and halohydrocarbons, such as methylene chloride or chlorobenzene. It is also possible to use aqueous organic two-phase systems, such as $H_2O$/toluene or $H_2O$/clorobenzene.

Preferably used bases are low molecular weight alcoholates, for example alkali metal alcoholates, such as sodium methylate or sodium ethylate, and alkali metal hydroxides, e.g. sodium hydoxide or potassium hydroxide, when a two-phase system is used. Bases such as butyllithium, alkali metal hydrides or alkali metal amides can also be used, the reaction being arried out, if necessary, under a protective gas.

The amount of base is not particularly critical; usually, a stoichiometric amount of the base or a small excess, for example from 1 to 20 mol % excess, is used per mole of phosphonium halide. Larger amounts are possible but generally have no further advantages.

A stoichiometric amount or, advantageously, a small excess, for example from 10 to 20 mol % excess, of the ylides III or VI can be used per mole of the aldehydes II or V used for the Wittig reaction. Larger or smaller amounts are possible.

The α,β-unsaturated acetal IV formed after the first Wittig reaction is obtained as a cis/trans mixture and is converted into the pure trans-aldehyde V in the subsequent cleavage of the acetal by acid hydrolysis.

Suitable acids are mineral acids or organic acids, such as carobxylic acids, dicarboxylic acids or sulfonic acids. Examples are hydrochloric acid, acetic acid, oxalic acid and toluenesulfonic acid. Usually from 1 to 2 acid equivalents are used per mole of acetal IV. Advantageously, the treatment with dilute hydrochloric acid, for example from 5 to 30% strength hydrochloric acid, is carried out at from 0° to 50° C. in an inert solvent, for example an ether, such as diethyl ether, methyl tert-butyl ether r tetrahydrofuran.

In the subsequent second Wittig reaction which is known per se from the literature, for example from French Laid-Open Application 2,505,820, the desired diene I is obtained in an E2/EE ratio of about 85:15 and may be isolated in a conventional manner and, for example, purified by column chromatography.

An advantage of the novel process is that it can be carried out in a simple manner. For exmaple, the intermediates obtained can be used for the subsequent stages without expensive purification steps. Phosphine oxide formed in the Wittig reactions need not be separated off until the end of the reaction sequence.

The Examples which follow illustrate the process.

EXAMPLE 1

Preparation of the trans-2-nonenals V 172 g (1.0 mole) of 7-acetoxyheptanal and 514 g (1.2 moles) of (1,3-dioxolan-2-yl)-methyltriphenylphosphonium bromide in 3 l of dimethylformamide are heated to 90° C., and 65 g (1.2 moles) of sodium methylate are added a little at a time. The mixture is stirred for a further 6 hours at 90° C. and cooled, after which it is worked up by adding 6 l of water and extractign with methyl tert-butyl ether. Washing and drying give 243 g of a product mixture, which is taken up in 300 ml of tetrahydrofuran, and 300 ml of 10% strength hydrochloric acid are added. The mixture is stirred for 3 hours at room temperature, and 500 ml of water are added, after which the mixture is extracted with methyl tert-butyl ether and the organic phase is washed and dried.

187 g of a product mixture are obtained, gas chromatographic analysis showing that this mixture consists of 47% of 9-hydroxy-2-nonenal and 18% of 9-acetoxy-2-nonenal; this corresponds to a total yield of 73%. The crude product can be used directly for the following reactions, i.e. the Wittig reaction and any esterification of the free OH group.

EXAMPLE 2

Conversion of 9-acetoxy-2-nonenal to E7/Z9-dodecadienyl acetate 385 g (1.00 mole) of propyltriphenylphosphonium bromide in 3 l of tetrahydrofuran are initially taken, and 112 g (1 mole) of potassium tert-butylate are added a little at a time. The mixture is stirred for 30 minutes at room temperature, after which 217 g (0.835 mole) of 9-acetoxy-2-nonenal (76% strength, crude product) are added dropwise and stirring is continued for 45 minutes at room temperature. The reaction is terminated by adding 500 ml of $H_2O$. The mixture is worked up by adding NaCl solution, extracting with diethyl ether and drying over $Na_2SO_4$; the crude product is then filtered over silica gel using 1:1 ethyl acetate/petroleum ether. 242 g of product are obtained, gas chromatographic analysis showing that this product consists of 24% of E7/Z9-dodecadienol and 44% of E7/Z9-dodecadienyl acetate.

60 ml (0.63 mole) of acetic anhydride and 65 ml (0.80 mole) of pyridine are added to this mixture and refluxing is carried out for 3 hours. The addition of ice water, extraction with methylene chloride, washing of the organic phase with 1% strength hydrochloric acid and water and drying over $Na_2SO_4$, give 259 g of a product mixture which, according to gas chromatographic analysis, contains 69.2% of E7/Z9-dodecadienyl acetate; this corresponds to a total yield of 96%.

Further purification is carried out by distillation.

We claim:

1. A process for the preparation of a compound of the formula I

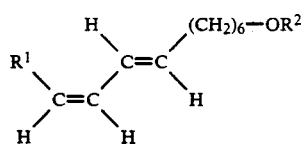

where $R^1$ is $C_1$–$C_8$ alkyl and $R^2$ is hydrogen or a base-stable alcohol protective group, wherein a 7-hydroxyheptan-1-al, which may be protected at the OH function, of the formula II

$$OHC-(CH_2)_6-OR^2 \qquad II$$

is subjected to a Wittig reaction with a phosphorylide of the formula III

where $R^3$ and $R^4$ are each a low molecular weight alkyl group or are bonded to one another to form an unsubstituted or $C_1$–$C_4$-alkyl-substituted dioxan or dioxolan system and $R^5$ is alkyl, cycloalkyl, phenyl or substituted phenyl, to give a compound of the formula IV

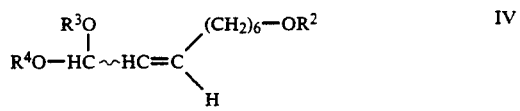

which is converted by the action of an acid into a trans-2-nonenal of the formula V

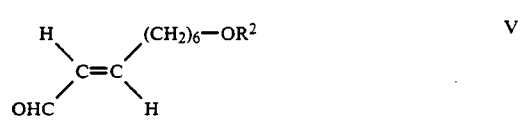

which is converted by a further Wittig reaction with a phosphorylide of the formula VI

where $R^1$ and $R^5$ have the abovementioned meansings, to a compound of the formula I, wherein said base-stable alcohol protective grou $R^2$ is $C_4$–$C_{12}$-tert-alkyl carrying a tertiary carbon atom in the 1-position, $C_3$–$C_8$-trialkylsily, benzyl, $C_2$–$C_4$-alkanoyl, benzoyl, $C_2$–$C_9$-alkoxymethoxy, $C_3$–$C_{10}$-1-alkoxyethoxy, 2-furanyl, 2-tetrahydrofuranyl, 2-pyranyl, 2-tetrahydropyranyl, 1,3-dioxan-2-yl or 1,4-dioxan-2-yl.

2. A process as claimed in claim 1, wherein the alcohol protective group $R^2$ used is acetyl.

3. A process as claimed in claim 1, wherein $R^5$ in the phosphorylie III is phenyl.

4. A process as claimed in claim 1, wherein the Wittig reactions are carried out in an aprotic solvent.

5. A process as claimed in claim 1, wherein the acid used is dilute hydrochloric acid.

6. A process as claimed in claim 1, wherein the acid is allowed to act on he acetal IV at from 0° to 50° C.

7. A process as claimed in claim 1, wherein from 1 to 2 acid equivalents are used per mole of acetal IV.

* * * * *